United States Patent [19]

Bilgutay

[11] Patent Number: 4,517,986
[45] Date of Patent: May 21, 1985

[54] FOUR FUNCTION VITAL SIGN MONITOR

[76] Inventor: Ilhan M. Bilgutay, 1063 Cephas Rd., Clearwater, Fla. 33575

[21] Appl. No.: 586,550

[22] Filed: Mar. 5, 1984

[51] Int. Cl.³ .............................................. A61B 5/02
[52] U.S. Cl. ................... 128/671; 128/680; 128/689; 128/683
[58] Field of Search ............... 128/672, 677, 670-671, 128/680-683

[56] References Cited

U.S. PATENT DOCUMENTS

| | | | |
|---|---|---|---|
| 4,009,709 | 3/1977 | Link et al. | 128/681 |
| 4,074,711 | 2/1978 | Link et al. | 128/681 |
| 4,137,907 | 2/1979 | Jansen et al. | 128/681 |
| 4,154,238 | 5/1979 | Link | 128/681 |
| 4,174,707 | 11/1979 | Link et al. | 128/681 |
| 4,270,547 | 6/1981 | Steffen et al. | 128/671 |
| 4,367,751 | 1/1983 | Link et al. | 128/681 X |
| 4,383,534 | 5/1983 | Peters | 128/671 |

Primary Examiner—Lee S. Cohen
Assistant Examiner—Angela D. Sykes
Attorney, Agent, or Firm—Ronald E. Smith; Miguel A. Valdes

[57] ABSTRACT

A four function vital sign monitor. The apparatus provides a display showing a person's temperature, respiration rate, pulse rate and blood pressure. The apparatus is specifically designed to provide accurate systolic and diastolic measurements for persons having healthy, flexible arteries or unhealthy, rigid arteries, or having unusually low blood pressure as a result of trauma or other shock-inducing event. A blood pressure cuff applied around any extremity transmits cuff pressure signals, for blood pressure and pulse rate computation, to a pressure transducer housed in the monitor. The versatility of the apparatus resides in its provision of a plurality of devices having different levels of sensitivity so that pressure pulses of differing amplitudes transmitted by the pressure transducer are detected by different ones of such detecting devices. Each device, when activated by a pressure pulse having the requisite threshold amplitude, emits a signal to a microprocessor that computes the diastolic and systolic pressure and the pulse rate. When any one or more of the pressure pulses of an individual are not present, the microprocessor performs computations on the available data as modified by the addition of predicted values for the unavailable data. When pressure signals even smaller than a preselected allowable threshold are present, a threshold-establishing device is automatically bypassed to admit such small signals to the microprocessor through the amplifiers.

16 Claims, 2 Drawing Figures

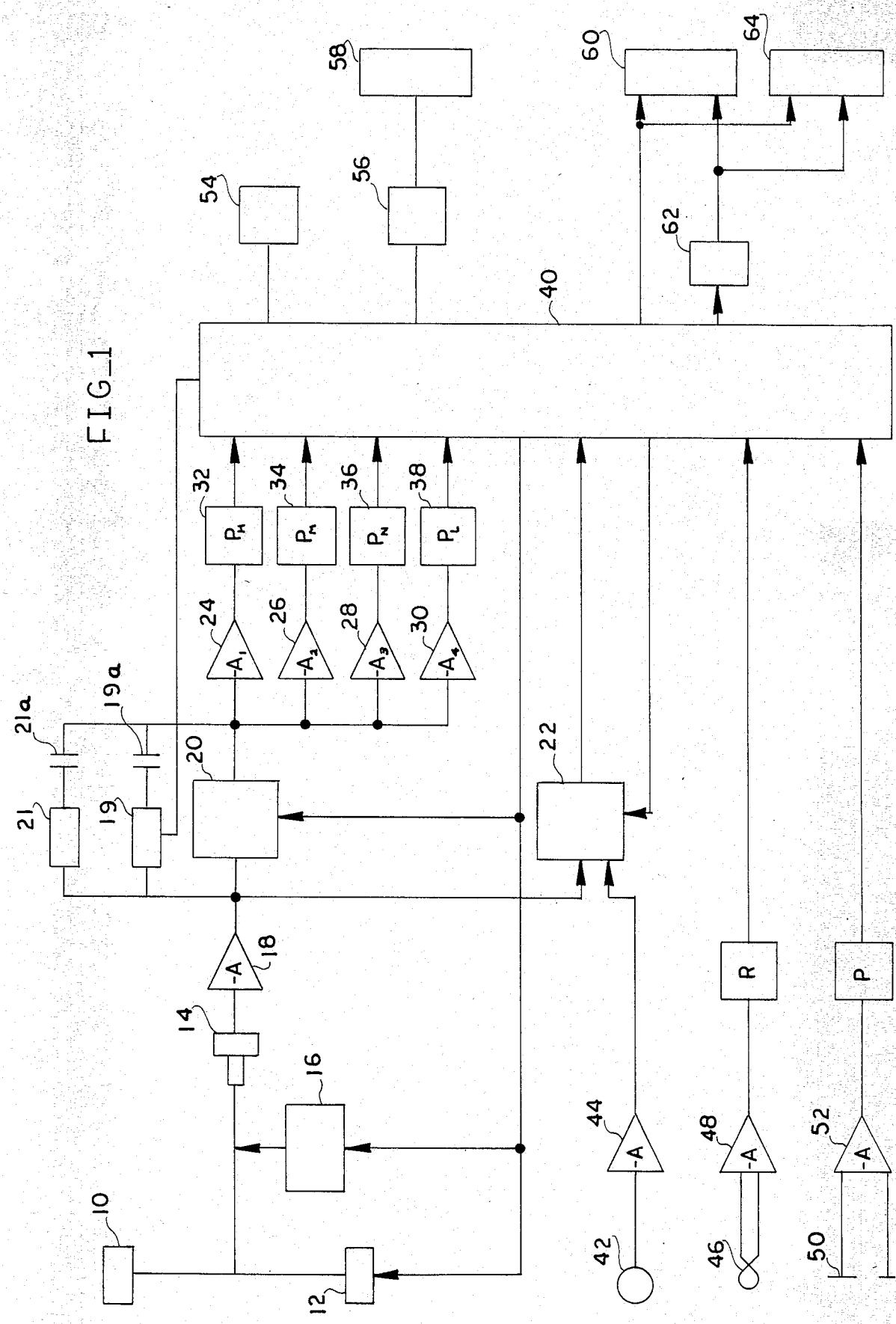
FIG_1

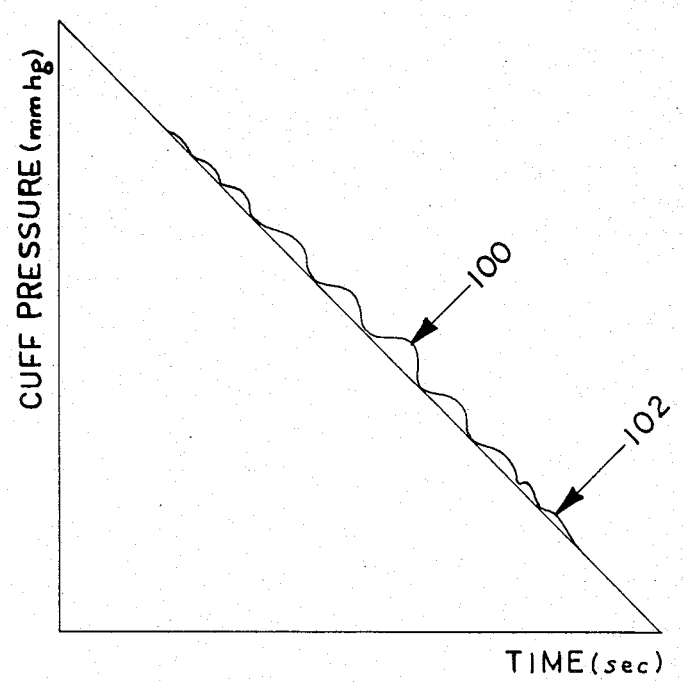
FIG_2

FOUR FUNCTION VITAL SIGN MONITOR

BACKGROUND OF THE INVENTION

1. Field of the Invention

This invention relates to monitoring systems, and more particularly, to an apparatus that monitors the vital signs, i.e., pressure, pulse rate, respiration rate and temperature of an individual.

2. Description of the Prior Art

With respect to blood pressure, there are two major measuring methods commonly used: (1) Auscultory method; (2) Oscillometric method. The auscultory method uses a piezoelectric transducer, which is inserted in a cuff to be positioned on the brachial artery of the person whose vital signs are being monitored. Because piezoelectric transducers respond to sound waves, sound signals from this artery are detected corresponding to first and last pressure pulses. These pulses are thereafter processed to determine systolic and diastolic pressures, respectively. The main disadvantage of this method is the critical positioning of the transducer on the brachial artery. If not properly positioned, the blood pressure readings are consequently affected. If the operator is untrained, careless, or does not realize the importance of correct placement, incorrect readings are likely to result.

The oscillometric method constitutes an improvement over the auscultory method because cuff positioning around the arm does not require any special precautions. The cuff is employed to transmit pressure pulses to a transducer located within a monitoring apparatus, there being no transducer in the cuff itself. In using this method, the first detectable systolic pressure pulse and the largest pressure pulse at the lowest cuff pressure corresponding to the mean arterial pressure is detected. From this value the diastolic pressure is computed by complex equations. In order to obtain the systolic pressure pulse and the largest pressure pulse, the stop-deflate approach is normally used. In this approach, the cuff is inflated to a certain known pressure level, such as 170 mmhg. The cuff is then deflated approximately 7 mmhg and the deflation is stopped to search for pressure pulses. In the absence of pressure pulses, the deflation-stop routine is repeated, again and again. Eventually, the first recognizable systolic and the largest pressure pulse is detected. Using the cuff pressure value at which time these values occur, diastolic pressure is determined. A significant disadvantage of this approach is that the computed and the actual diastolic pressures do not closely coincide. Furthermore, it is undesireable for a person whose vital signs are being monitored to have one arm under pressure for prolonged periods of time. It is also important to note that in cases where the pressure pulses of the individual whose vital signs are being monitored are all of low amplitude, it is very difficult to detect a maximum amplitude pulse from among all the pulses. Thus, the mean pressure upon which all succeeding calculations are based is very likely to be incorrect. Even more important to note is the fact that prior art devices detect the systolic and mean arterial pressures first, and then calculate the diastolic pressure from said systolic and mean arterial pressure. Since the systolic and mean arterial pressure detection are often erroneous, and since the diastolic pressure is calculated from these values, it is clear that errors are added upon errors in arriving at the diastolic pressure determination. This is highly objectionable, because the diagnosis of ailments of the heart and kidney, for example, rely heavily on diastolic pressure values.

A better approach using this method is to detect the first and last pressure pulses corresponding to the true systolic and diastolic pressures as the cuff is continuously deflated without interruption. However, an awkward problem is encountered in this approach while detecting pressure pulses with audible sound. The audibility of pressure pulses is affected by the pulse amplitude as well as by the rigidity of the brachial artery wall. In some persons with hardened arterial walls, the pressure pulses generate audible sound although the pulse amplitude is very small. In contrast, other persons with very smooth and flexible arterial walls require very large amplitude pressure pulses to generate audible sound.

There is thus a need for a vital sign monitor with the capability of accurately determining pressure values on persons with all kinds of arterial wall conditions.

It is therefore an object of this invention to provide a vital sign monitor that computes pressure, pulse, respiration and temperature and which displays the values automatically.

It is another object of the present invention to provide a vital sign monitor that computes accurately and very quickly blood pressure values of any person regardless of age, size, height and artery condition.

It is still another object of the present invention to provide a vital sign monitor with sufficient sensitivity to detect any range of pressure pulses in any individual.

It is a further object of the invention to provide a vital sign monitor that computes systolic and diastolic pressures by using continued and uninterrupted cuff deflation, thereby assuring speed and comfort to the person whose vital signs are being monitored.

SUMMARY OF THE INVENTION

This invention accomplishes these and other objects by providing a vital sign monitor having a hardware system that receives input signals from a pressure transducer and a thermistor or thermocouple. A temperature probe connected to the monitor houses the thermistor on its tip to measure and monitor temperature readings. Also, thermistor beads housed on the probe handle provide exhale signals to the monitor. A pressure transducer is housed in the monitor. The transducer detects two kinds of signals: (1) cuff dynamic pressure pulse signals for systolic and diastolic pressure computation, and for the pulse rate computation as well, and (2) a static pressure signal which is directly proportional to the applied cuff pressure. In addition, the pulse rate may also be monitored independently of the transducer. All these signals are then amplified to proper levels and by passing through filters and signal conditioners they are fed into a microprocessor that produces final results by straightforward analysis and computations. This monitor also has a software system which includes a series of instructions located in an erasable memory unit. Under the sequential command of these instructions, the microprocessor performs the necessary computations and logic functions to provide final results to the operator.

This invention measures blood pressure by using a unique approach. As mentioned above, the pressure transducer provides two types of signals. One is the static output or pressure signal which is directly proportional to the applied cuff pressure. The range of this signal is generally from 0 to 300 mmhg. This signal is fed into an operational amplifier whose output in turn is fed into an analog to digital converter. The A/D converter output is fed into the microprocessor and by special program instructions, the transducer pressure signal is displayed in digital form on a display module. This output is calibrated against a known mercury manometer reading.

The other signal has the form of minute pulses overriding the static pressure level signal. When the cuff wrapped around the arm is inflated to a certain pressure value, the brachial artery on the arm above the elbow becomes occluded. The cuff pressure is then released gradually at a rate of 3-7 mmhg/second, approximately. At a certain cuff pressure, a first pressure pulse is transmitted which is followed by a second pressure pulse, a third, a fourth, and so on. As the pressure pulses get stronger, i.e., as they increase in amplitude, the static pressure values diminish. The plurality of static pressure values at which these dynamic pressure pulses appear are algebraically summed and averaged to obtain the systolic blood pressure. This average value very closely relates to the first sound heard by the auscultory method. The dynamic pressure pulses increase until they hit a peak amplitude, after which they start losing strength with continued decreasing cuff pressure. The static pressure values at which the dynamic pressure pulses disappear are again algebraically summed and averaged to obtain the diastolic pressure. This averaging is an important feature of the invention and is performed to avoid errors introduced in the pressure computation due to various arterial wall conditions. The systolic pressure is the average value of the cuff pressures at which all pressure pulses from the smallest to the highest start transmission. The diastolic pressure is the average value of the cuff pressures at which all pressure pulses from the highest to the smallest end transmission.

Other objects, features, and advantages of the present invention will become apparent from the following detailed description taken in conjunction with the accompanying drawings.

BRIEF DESCRIPTION OF THE DRAWINGS

FIG. 1 is a simplified block diagram of one embodiment of the vital sign monitor according to the present invention, and FIG. 2 illustrates the static cuff pressure output and minute dynamic pressure pulses provided by the transducer of the present invention.

DETAILED DESCRIPTION OF THE PREFERRED EMBODIMENT

Referring now to FIG. 1, reference numeral 10 denotes a cuff, 12 a cuff inflating means, 14 a pressure transducer, 16 a deflation rate control valve, 18 a preamplifier, 24, 26, 28 and 30 denote operational amplifiers; 20 a discriminator, 19 and 21 relay means, 19a and 21a capacitor means, 22 an analog to digital converter; 32, 34, 36 and 38 denote one-shot generators, 40 a microprocessor, 42 a thermistor, 46 thermistor beads, 50 an independent pressure pulse detector, 44, 48 and 52 denote operational amplifiers; 54 a printer or tape device; 56 a display driver; 58 a display device; 60 an erasable programmable memory; 62 an address decoder and 64 a random access memory.

As shown in FIG. 2, 100 denotes a number of minute dynamic pressure pulses transmitted by pressure transducer 14 of FIG. 1. Pulses 100 override the applied cuff pressure denoted as 102. Referring again to FIG. 1, pulses 100 are amplified by preamplifier 18 which sends its output signals to discriminator 20. The function of discriminator 20 is to differentiate among incoming pressure pulses so that only pulses above a preselected minimum amplitude are allowed to pass through as output to operational amplifiers 24, 26, 28 and 30. Also, the sensitivity of these amplifiers is adjusted to respond to small, medium, normal and high amplitude pulses, respectively. As an example, operational amplifier 24 will respond to the small signals coming from the transducer 16 via the discriminator 20. The amplifier 24 output is then sent to one-shot generator 32 which in turn provides a noise free square pulse to the microprocessor 40 to indicate the transmission of this small pressure pulse.

When computing the blood pressure of an individual, this embodiment operates as follows.

First, the cuff 10 is inflated by the inflate means 12 to a pressure between 190-200 mmhg. The cuff may be placed at any extremity, there being no need to limit placement thereof to any specific artery such as the brachial artery. The cuff 10 will start deflation at a rate of 4-6 mmhg. At a certain cuff pressure P(H), the first small pressure pulse H is transmitted, overriding cuff 10 pressure. Next, the medium pulse signals M start transmission at cuff pressure P(M) along with the small signals H. At this point, the monitor increases the deflation rate by means of the deflation rate control 16. Because the deflation normally decreases when the cuff pressure decreases, a higher deflation rate is introduced automatically to keep a constant deflation on the monitor. Later, as cuff pressure continues decreasing, the normal pressure pulses N start transmission at cuff pressure P(N). Finally, the high pressure pulses L start transmission at cuff pressure P(L) and the average of the cuff pressures [P(H), P(M), P(N), and P(L)] is automatically computed by microprocessor 40. This value is the average systolic pressure. An example of the computed systolic pressure is the following:

P(H)=150; p(M)=135; P(N)=120; P(L)=105
Average Systolic Pressure=(150+135+120+105)/4=127

Subsequently, as cuff 10 continues deflation, the pressure pulses end their transmission. At cuff pressure P(LD), pressure pulse L transmission is ended. Likewise, pressure pulse N, M, and H transmission ended at cuff pressures P(ND), P(MD) and P(HD). After H ends transmission, the monitor holds its operation for a few seconds to assure that no additional pulses are detected. Immediately after this short waiting period an average of the four cuff pressures [P(LD), P(ND), P(MD) and P(HD)] is automatically computed. This value is the average diastolic pressure. An example of the computed diastolic pressure is the following:

P(LD)=90; P(ND)=80; P(MD)=70; P(HD)=60
Average Diastolic Pressure=(60+70+80+90)/4=75

Accordingly, the computed blood pressure from the above examples is 127/75.

The value for the medium pulse signal M is also employed to reinflate the cuff if M appears above 160 mmhg (160 mmhg is the accepted borderline for high blood pressure). When M is detected above 160 mmhg, as is common in individuals with high blood pressure, the monitor immediately reinflates the cuff, not waiting for the cuff pressure to deflate to its minimum level, and the deflate routine is followed again. If M is still present above the accepted level, the monitor reinflates to its maximum 255 mmhg and the regular deflate routine, described above, is followed.

In some persons, the pressure pulses are very weak, and only M and H are present. This embodiment will compute an average of P(M) and P(H) values in such situations. However, an expected P(N) value may be included with the P(M) and P(H) values, to achieve better averaging. P(N) is estimated as P(M) less a constant. The technique of including an estimated value for a missing pressure pulse to achieve a better averaging is employed in all applicable embodiments of this invention. For example, where P(H) only is present, an estimated value for P(M) can be arrived at by subtracting a constant from the value of P(H), and where P(H), P(M) and P(N) are present, an estimated value for P(L) can be included to provide a good averaging of values.

In very extreme cases such as those involving a person having very low pressure conditions, H only may be present. Although in these cases P(H) and P(HD) may be used as systolic and diastolic pressure values, respectively, for a more accurate reading a predicted value is assigned to P(M) and P(MD). For example, for given P(H) and P(HD) values, it is assumed that P(M) is 15 mmhg lower than P(H) and P(MD) is 15 mmhg higher than P(HD). Hence, the equations to compute the heart pressure with this embodiment are as follows:

Average Systolic Pressure=$[P(H)+(P(H)-15)]/2$

Average Distolic Pressure=$[P(HD)+(P(HD)-15)]/2$

The monitor is also provided with a means to bypass the discriminator 20 in some situations where even P(H) may not be present. If no H pressure pulse is detected when the applied cuff pressure decreases from 195 mmhg to a preselected level such as 125 mmhg or so, then the microprocessor 40 trips relay means 19 so that a signal may be fed to the op amps 24, 26, 28 and 30, directly bypassing the discriminator through capacitor 19a. This provides a detection level sufficient to even pick up pulses that are only found in extremely weak pulse or shock situations. Alternatively, the operator of the monitor may manually trip relay 21, and cause the signals to be fed to the op amps through capacitor 21a, at choice.

As mentioned before, H pulses are always present in all persons. This embodiment uses H pulses to compute the pulse rate of a person. When the first small pulse H1 is transmitted, it is discarded and further small pulses, H2, H3, etc., are used for the computation. From the wave period [P(H2)−P(H3)] the instantaneous pulse rate is computed. Then the next instantaneous pulse rate is computed from wave period [P(H3)−P(H4)]. If both pulse rates are within plus or minus three of each other, P(H2) is taken as the cuff pressure at which pressure pulse H transmission starts and the computed pulse rate [P(H2)−P(H3)] as the heart rate. On the contrary, if the compared pulse rates are not within plus or minus three of each other, P(H2) is discarded and subsequent pulse rates are compared until the values fall within the limits. This process is continued until P(H) pulses disappear. Obtained individual pulse rates are averaged during the blood pressure monitoring process and when P(H) disappears, average pulse rates are shown.

This digital filtering for obtaining pulse rates is also utilized to filter out the artifact due to movement at high pressure range (arm movement, e.g., may produce irregularities). If arm movement occurs, H pulses are erratic and thus eliminated. As soon as irregularities subside, initial pulse rate is captured as is the P(H) value.

A synergistic result of the simple but highly effective inventive means to calculate systolic and diastolic pressures as above-described is attributable to the savings realized in the available memory of the microprocessor. With excess memory, vis a vis the memory that would be available in prior art monitors, the microprocessor is able to perform the temperature and respiration rate computations on a time-sharing basis with the blood pressure computations.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. An apparatus of the type designed to monitor the vital signs of a person, comprising,
    a cuff to exert pressure on any preselected artery of a person,
    means for inflating and deflating said cuff,
    means for controlling the deflation rate of said cuff so as to maintain the rate at a substantially constant value during the deflation of said cuff,
    a transducer coupled to said cuff which transmits pressure signals proportional to the pressure of said cuff and pressure pulses from said artery,
    an analog to digital converter responsive to pressure signals from said transducer to convert said pressure signals to digital representations,
    a plurality of amplifiers coupled to said transducer and respectively responsive to pressure pulses having the smallest amplitude, the highest amplitude and amplitudes therebetween, for providing transmission indications of said pressure pulses,
    a microprocessor coupled to said analog to digital converter and said amplifiers to receive transmission indications of said pressure pulses and digital representations of the pressures at which said pressure pulse transmissions start and end, so as to compute the systolic and diastolic pressure, and
    means associated with said microprocessor for displaying the systolic and diastolic pressure values.

2. A vital sign monitoring apparatus as recited in claim 1, wherein said plurality of amplifiers comprises,
    a first amplifier means for amplifying small amplitude pressure pulses,
    a second amplifier means for amplifying medium amplitude pressure pulses,
    a third amplifier means for amplifying normal amplitude pressure pulses, and
    a fourth amplifier means for amplifying high amplitude pressure pulses.

3. A vital sign monitor as recited in claim 2, further comprising reinflating means that reinflates said cuff upon detection of a pressure pulse of medium amplitude that is above a preselected acceptable pressure level, said reinflating means effecting said reinflation substantially immediately upon said detection of a medium pressure pulse of unacceptably high amplitude, without delaying such reinflation until said cuff has deflated to a minimum pressure.

4. A vital sign monitoring apparatus as recited in claim 1, wherein said microprocessor computes the person's pulse rate with the transmission indications of the pressure pulses having the smallest amplitude values and the digital representations of the pressures at which said pulse transmission starts, and wherein said vital sign monitoring apparatus further comprises means associated with said microprocessor for displaying the pulse rate.

5. A vital sign monitoring apparatus as recited in claim 4, further comprising means associated with said microprocessor for printing said pulse rate value.

6. A vital sign monitoring apparatus as recited in claim 1, further comprising means associated with said microprocessor for printing said systolic and diastolic values.

7. A vital sign monitoring apparatus as recited in claim 1, further comprising a discriminator means coupled to said transducer to limit the pulse transmission to pressure pulses above a preselected minimum value.

8. A vital sign monitoring apparatus as recited in claim 7, further comprising a preamplifier coupled between said transducer and said discriminator means which amplifies the pressure pulses transmitted from said transducer.

9. A vital sign monitor as recited in claim 7, further comprising a discriminator by-pass means so that pressure pulses having amplitude values less than the threshold amplitude established by said discriminator means are processed by said microprocessor when said discriminator means is by-passed.

10. A vital sign monitor as recited in claim 9, wherein said discriminator by-pass means is controlled by said microprocessor and wherein said discriminator by-pass means is activated by said microprocessor responsive to the absence of discriminator means passed pressure pulses attendant cuff deflation to a preselected pressure.

11. A vital sign monitor as recited in claim 9, wherein said discriminator by-pass means is manually activated.

12. A vital sign monitor as recited in claim 1, further comprising,
a temperature probe for monitoring the temperature of an individual,
said temperature probe having a handle which houses means for monitoring the respiration rate of an individual,
means for monitoring the pulse rate of an individual, said pulse rate monitoring means including said microprocessor, and
said microprocessor adapted to compute and cause to be displayed said systolic and diastolic blood pressure values, said temperature, said respiration rate, and said pulse rate in a substantially simultaneous manner.

13. A method for computing the blood pressure of a person, in a vital sign monitoring apparatus comprising a cuff, a transducer, an analog-to-digital converter, first, second, third and fourth amplifiers and a microprocessor, including the steps of:
exerting pressure with said cuff on any preselected artery of the person;
transmitting pressure signals proportional to the pressure of said cuff by said transducer;
transmitting pressure pulses from the artery by said transducer;
providing transmission indications of pressure pulses with small amplitude by said first amplifier;
providing transmission indications of pressure pulses with medium amplitude by said second amplifier;
providing transmission indications of pressure pulses with normal amplitude by said third amplifier;
providing transmission indications of pressure pulses with high amplitude by said fourth amplifier;
converting the pressure signals to digital representations by said analog-to-digital converter;
receiving by said microprocessor the transmission indications of pressure pulses with small, medium, normal and high amplitudes and the digital representations of the pressure signals;
averaging by said microprocessor of the digital representations of the pressures at which the pressure pulses with small, medium, normal and high amplitudes start transmission to determine the systolic pressure; and
averaging, by said microprocessor, the digital representations of the pressures at which the pressure pulses with small, medium, normal and high amplitudes end transmission to determine the diastolic pressure.

14. A method for computing blood pressure of a person with low pressure pulse, in a vital sign monitoring apparatus comprising a cuff, a transducer, an analog-to-digital converter, first and second amplifiers, and a microprocessor, including the steps of:
exerting pressure with said cuff on any preselected artery of the person;
transmitting pressure signals proportional to the pressure of said cuff by said transducer;
transmitting pressure pulses from the preselected artery by said transducer;
providing transmission indications of pressure pulses with small amplitude by said first amplifier;
providing transmission indications of pressure pulses with medium amplitude by said second amplifier;
converting the pressure signals to digital representations by said analog-to-digital converter;
receiving by said microprocessor the transmission indications of pressure pulses from said first and second amplifiers and the digital representations from said analog-to-digital converter;
averaging by said microprocessor the digital representation of the pressures at which the pressure pulses with small and medium amplitudes start transmission to determine systolic pressure; and
averaging by said microprocessor the digital representation of the pressures at which the pressure pulses with small and medium ampliutudes end transmission to determine diastolic pressure.

15. A method for computing blood pressure of a person in shock, in a vital sign monitoring apparatus comprising a cuff, a transducer, an analog-to-digital converter, a first amplifier and a microprocessor, including the steps of:
exerting pressure with said cuff in any preselected artery of the person;
transmitting pressure signals proportional to the pressure of said cuff by said transducer;

transmitting pressure pulses from said artery by said transducer;
providing transmission indications of pressure pulses with small amplitude by said first amplifier;
converting the pressure signals to digital representations by said analog-to-digital converter;
receiving by said microprocessor the transmission indications of pressure pulses from said first amplifier and the digital representations from said analog-to-digital converter;
averaging by said microprocessor of the digital representation of the pressure at which the pressure pulses with small amplitude start transmission plus the value of said representation minus a known constant to determine systolic pressure; and
averaging by said microprocessor of the digital representation of the pressure at which the pressure pulses with small amplitude end transmission plus the value of said representation plus said known constant to determine diastolic pressure.

16. A method for computing the heart rate of a person, in a vital sign monitoring apparatus comprising a cuff, a transducer, an analog-to-digital converter, a first amplifier and a microprocessor, including the steps of:
exerting pressure with said cuff on any preselected artery of the person;
transmitting pressure signals proportional to the pressure of said cuff by said transducer;
transmitting pressure pulses from said artery by said transducer;
providing transmission indications of pressure pulses with small amplitude by said first amplifier;
converting the pressure signals to digital representation by said analog-to-digital converter;
receiving by said microprocessor the transmission indications of pressure pulses from said first amplifier and the digital representations from said analog-to-digital converter;
discarding the digital representation of the first transmitted pressure pulse with small amplitude;
determining a first pulse rate by computing the wave period between the second and third pressure pulses with small amplitude, as the difference between the two digital representations at which said second and third pressure pulses start transmission;
determining a second pulse rate by computing the wave period between the third and fourth pressure pulses with small amplitude, as the difference between the two digital representations at which said third and fourth pressure pulses start transmission; and
comparing the differences between the first and second pulse rates with a number plus or minus a preselected constant to consider the first pulse rate as the heart rate if said difference is less than the number plus or minus said preselected constant such as three.

* * * * *